United States Patent [19]

Parris

[11] Patent Number: 4,546,204

[45] Date of Patent: Oct. 8, 1985

[54] PROCESS FOR THE MANUFACTURE OF METHYL T-BUTYL ETHER

[75] Inventor: David Parris, Nunawading, Australia

[73] Assignee: Imperial Chemical Industries Australia Limited, Melbourne, Australia

[21] Appl. No.: 665,973

[22] Filed: Oct. 29, 1984

[30] Foreign Application Priority Data

Nov. 7, 1983 [AU] Australia .............................. PG2244

[51] Int. Cl.$^4$ ............................................. C07C 41/05
[52] U.S. Cl. .................................. 568/697; 585/314; 585/662
[58] Field of Search ......................................... 568/697

[56] References Cited

U.S. PATENT DOCUMENTS 4,329,516 5/1982 Al-Muddarris ...................... 568/697
4,423,251 12/1983 Pujado et al. ....................... 568/697

Primary Examiner—Howard T. Mars
Attorney, Agent, or Firm—Cushman, Darby & Cushman

[57] ABSTRACT

The invention concerns a process for the manufacture of methyl t-butyl ether in which: a hydrocarbon feedstock is cracked to give an ethylene-rich stream; an isobutane-rich stream is separated from $C_4$-hydrocarbon stream; the ethylene-rich stream and the isobutane-rich stream are contacted over a transhydrogenation catalyst to give a mixture comprising ethane and isobutene; the isobutene is reacted with methanol to give methyl t-butyl ether; and the residual $C_4$-hydrocarbon stream is recycled either to the $C_4$-hydrocarbon stream or to the cracker and the ethane is recycled to the cracker.

It has been found that combining and interconnecting a hydrocarbon cracker, a transhydrogenation reactor and an etherification reactor results in an integrated, economic process for the production of methyl t-butyl ether.

12 Claims, 3 Drawing Figures

PROCESS FOR THE MANUFACTURE OF METHYL T-BUTYL ETHER

This invention relates to a process for the manufacture of methyl t-butyl ether (MTBE) and in particular to an integrated process for the manufacture of MTBE involving the use of a transhydrogenation reaction to produce isobutene.

With legislation in many countries requiring lead-free or reduced lead content gasoline there is a need for alternative additives which will boost the octane number of gasoline. Methyl t-butyl ether is a particularly attractive alternative additive because of its high octane number, miscibility with gasoline and its environmental acceptability.

Methyl t-butyl ether may be readily manufactured by the etherification of methanol with isobutene. However, only a limited supply of isobutene is available from hydrocarbon cracking and commercial processes have been proposed for the isomerization of n-butane from liquid petroleum gas to give isobutane and the dehydrogenation of the isobutane to give isobutene.

In the proposed commercial processes for the preparation of isobutene, and subsequently MTBE, the dehydrogenation of isobutane to give isobutene severely limits the economics of the overall process as the dehydrogenation reaction is thermodynamically unfavourable. The dehydrogenation reaction is highly endothermic and therefore requires significant expenditure on feed preheating, and the reaction must be carried out at high temperatures (typically 540° to 640° C.) and at reduced reactant partial pressures (typically under vacuum or with steam dilution) to drive the reaction.

It has now been found that by integrating a cracking facility producing ethylene with an etherification facility, isobutene may be produced for the manufacture of methyl t-butyl ether in a much more efficient manner by the transhydrogenation of isobutane using ethylene as a hydrogen acceptor and the recycling to the cracking facility of the ethane formed.

Accordingly the invention provides a process for the manufacture of methyl t-butyl ether which process comprises:

(i) cracking a hydrocarbon feedstock in a cracking facility to give an ethylene-rich stream;

(ii) separating an isobutane-enriched stream from a $C_4$-hydrocarbon stream and optionally isomerizing the n-butane and recycling the resulting $C_4$-hydrocarbon stream for separation;

(iii) contacting a mixture comprising the ethylene-rich stream from step (i) and the isobutane-enriched stream from step (ii) with a transhydrogenation catalyst to give a hydrocarbon mixture comprising isobutene and ethane;

(iv) either first separating the hydrocarbon mixture obtained in step (iii) into a $C_4$-hydrocarbon enriched stream comprising isobutene and a $C_2$-hydrocarbon enriched stream comprising ethane and second reacting said $C_4$-hydrocarbon enriched stream comprising isobutene with methanol to give methyl t-butyl ether and a residual $C_4$-hydrocarbon stream; or first reacting said mixture obtained in step (iii) with methanol to give methyl t-butyl ether and a residual hydrocarbon stream and optionally separating the residual hydrocarbon stream into a residual $C_4$-hydrocarbon stream and a $C_2$-hydrocarbon enriched stream; and (v) collecting the methyl t-butyl ether and recycling the residual $C_4$-hydrocarbon stream either to the $C_4$-hydrocarbon stream or to the cracking facility as feedstock and recycling the $C_2$-hydrocarbon enriched stream to the cracking facility or recycling the unseparated residual hydrocarbon stream to cracking facility.

The process of the present invention is particularly advantageous when the cracking facility used is a hydrocarbon cracker designed for the production of olefins. It will become clear to those skilled in the art that the production of methyl t-butyl ether using such a cracking facility has many advantages over prior art methods for the production of methyl t-butyl ether. For example, when a cracker based on liquified petroleum gas (LPG) feedstock is used in the process of the present invention: isobutane may be separated from the LPG to give a source of isobutane and an improved (lower isobutane content) feedstock for cracking; the ethylene from the cracker and the isobutane may be contacted with a catalyst to give isobutene and ethane in a transhydrogenation reaction at significantly lower temperatures and higher pressures than those used for prior art processes for the dehydrogenation of isobutane to give isobutene for methyl t-butyl ether production; the ethane may be separated and, as it is a particularly good cracker feedstock, recycled to the cracker; the isobutene may be etherified with methanol to give methyl t-butyl ether and any residual isobutane may be recycled for transhydrogenation. Thus the production of methyl t-butyl ether by the process of the present invention not only offers the advantage of lower capital cost because isobutene is produced at or above atmospheric pressure at significantly lower temperatures, but when integrated into an existing cracker unit enables the cracker to be run at design capacity to produce a high value product when ethylene demand is low.

Although the process of the present invention may be used to particular advantage when the cracking facility is a cracker designed primarily for the production of olefins it may also be used to advantage when the cracker is designed primarily for other purposes. For example, refineries which crack crude oil for the manufacture of petroleum products such as gasoline also produce "light" gas streams which contain ethylene. Such gas streams are often used as fuel gas and, because of the large operating scale of refineries, offer a convenient and economic source of ethylene for use in the transhydrogenation step of the process of the present invention.

Butanes are available in large quantities from liquified petroleum gas (LPG) produced during crude oil extraction and during crude oil refining. Isobutane for use in the process of the present invention may, for example, be obtained by separation from LPG or from a refinery $C_4$-hydrocarbon stream in a deisobutanization column. The remaining n-butane may be used as LPG or returned to the $C_4$-hydrocarbon stream as appropriate. Alternatively, the remaining n-butane may be partially isomerized to give an isobutane/n-butane mixture by passage over an isomerization catalyst and the mixture returned to the deisobutanization column for separation. However, if the cracking facility used in the process of the present invention is a cracker designed for olefin production the remaining n-butane may be used as cracker feedstock which has been improved for cracking by the removal of isobutane.

Suitable catalysts which may be used in the transhydrogenation step of the process of the present invention may be chosen from the dehydrogenation catalysts known in the art. Such dehydrogenation catalysts include heterogeneous catalysts such as, for example, supported and unsupported metals and metal oxides and mixtures thereof and homogeneous catalysts such as, for example, organometallic complexes.

Examples of metals which find use as dehydrogenation catalysts include metals from the Groups IVA, VA, VIA, VIIA, VIII, copper, zinc, gallium, indium, germanium, tin, lead, antimony, bismuth, tellurium and the oxides of certain of these metals. Such metals and their oxides may be used on their own as catalysts but are often mixed and used as mixed catalysts.

Examples of some of the preferred metals which find use as dehydrogenation catalysts include the platinum group metals platinum, palladium and nickel, the metals iridium, rhodium, cobalt, rhenium, ruthenium, iron and copper. These metals may be used as catalysts or their own or in combination either in admixture or in the form of alloys. The metals may also be used in combination, either in admixture or in the form of alloys, with other metals, metal oxides or promotors including, for example, metals such as the alkali metals, the alkaline earth metals, the rare earth metals and mixtures thereof, either in their elemental state or a higher oxidation state. Further the metals, or combinations thereof may be modified by poisoning, or reducing the activity thereof, by treatment with one of the poisoning agents known in the art. Such poisoning agents include, for example sulfur and compounds containing sulfur.

Examples of some of the preferred metal oxides which find use as dehydrogenation catalysts include the oxides of vanadium, chromium, molybdenum, copper, tungsten, titanium and zinc. These oxides may be used as catalysts on their own or in combination with other metal oxides or metals or promotors.

The metal and metal oxide catalysts which may be used in the transhydrogenation step of the process of the present invention may be unsupported, for example, in the form of a thin foil, a mesh, sponge, granules, pellets, finely divided powder or slurry. Alternatively, the metal and metal oxide catalysts which may be used in the transhydrogenation step may be supported on a carrier. If the catalysts which may be used in the transhydrogenation step are supported on a carrier, preferably the carrier is a porous carrier having a large surface area. Suitable carriers which may be used as catalyst supports in the transhydrogenation step include, for example, alumina, silica, aluminosilicates, zirconia, titania, active carbon and mixtures thereof.

Preferably, the catalysts used in the transhydrogenation step of the process of the present invention are non-acidic. Suitable non-acidic catalysts may be obtained either by selecting non-acidic catalysts and/or catalyst supports or by treating acidic catalysts and/or catalyst supports with organic or inorganic bases to poison the acidity of the catalyst and/or catalyst support.

The catalysts used in the transhydrogenation step of the process of the present invention may also be treated to alleviate undesirable properties and/or to improve the life of the catalyst, the surface area of the catalyst or the ease of regeneration of the catalyst. The properties of the catalyst may be modified by treating the catalyst or the catalyst support with one or more of the modifiers known in the art including, for example, sulfur and metals such as lead, tin, arsenic and antimony.

In the transhydrogenation step of the process of the present invention isobutane in the gaseous state may be contacted with the dehydrogenation catalyst by passing a gaseous mixture of isobutane and ethylene over a bed of dehydrogenation catalyst in an heterogeneous catalytic process. Alternatively, a mixture of isobutane and ethylene in the gaseous or liquid state may be contacted with a slurry of the dehydrogenation catalyst optionally in the presence of an inert solvent, again in an heterogeneous catalytic process. In a further alternative process, a mixture of isobutane and ethylene in the gaseous or liquid state may be contacted with a solution of, for example, an organometallic dehydrogenation catalyst in an inert solvent, in an homogeneous catalytic process.

One of the major advantages of the transhydrogenation step of the process of the present invention is that it may be carried out with good conversion and high selectivity at much lower temperatures and much higher pressures than the dehydrogenation processes currently used for the preparation of isobutene in the manufacture of methyl t-butyl ether. Preferably the transhydrogenation step of the process of the present invention is carried out at temperatures below 600° C., more preferably between 400° and 550° C., and at pressures close to or above atmospheric pressure, more preferably between 1.0 and 10 atmospheres.

In the etherification step of the process of the present invention methanol may be added to isobutene to give methyl t-butyl ether in an acid-catalysed reaction. For example, methyl t-butyl ether may be made in high yield by contacting a liquid phase mixture of methanol and isobutene with a solid phase acidic catalyst such as a strong acid ion-exchange resin.

BRIEF DESCRIPTION OF THE DRAWINGS

Specific embodiments exemplifying the use of the process of the present invention for the manufacture of MTBE will now be described, by way of example only, with reference to the accompanying drawings, wherein:

Referring to FIG. 1 of the drawings, liquified petroleum gas (11) is supplied to a deisobutanization unit (27) where it is separated (eg by distillation or selective adsorption) into an isobutane stream (13) and an n-butane rich stream (12). Optionally, all or part of the n-butane rich stream (12) may be fed to an isomerization unit (28) in which the n-butane is partially isomerized to isobutane by passage over an isomerization catalyst (eg a platinum containing isomerization catalyst at a temperature of 150° to 200° C.), and the n-butane/isobutane mixture returned to the deisobutanizer column (27). Optionally all or part of the n-butane rich stream (12)

Figure 1:
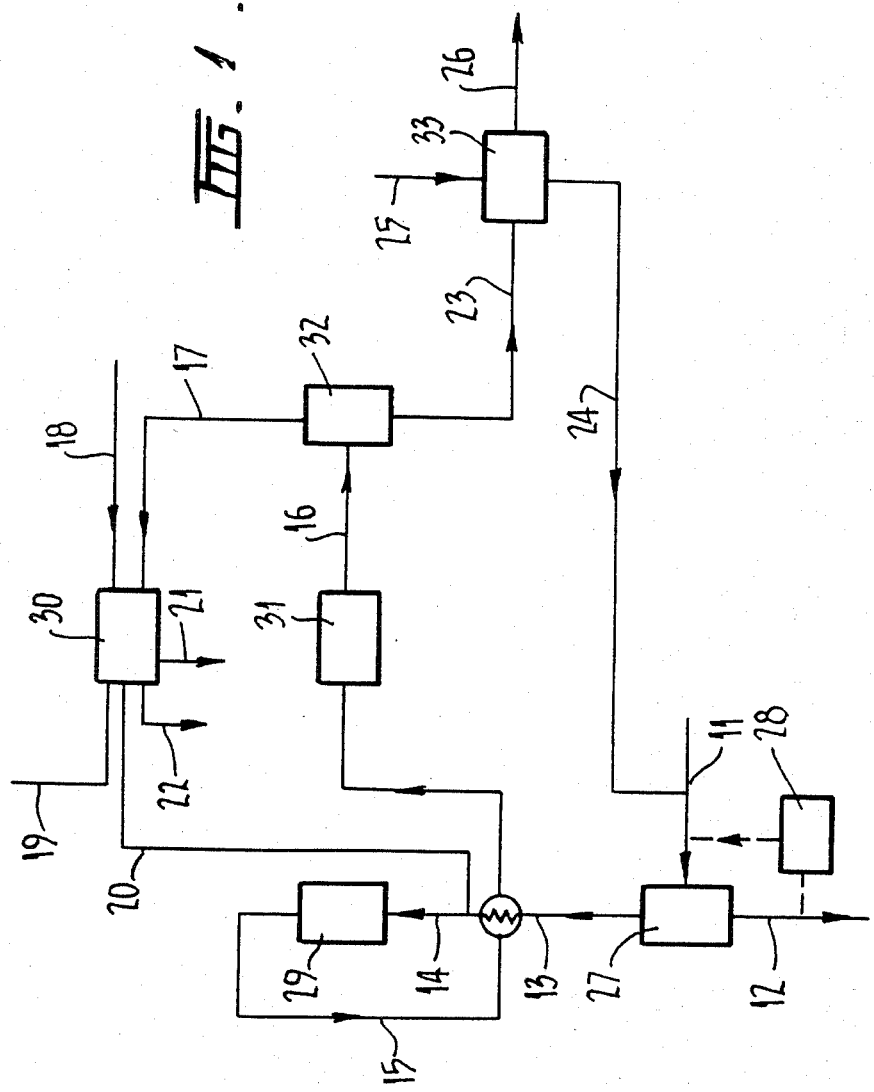
FIG. 1 is a schematic flow diagram of a plant for the production of MTBE using part or all of the ethylene output from a cracker, designed to predominantly produce ethylene and propylene by cracking naphtha or liquid petroleum gas, in the transhydrogenation of isobutane to isobutene.

may be used to form or supplement the make-up stream (18) fed to the catalytic cracker (30).

The isobutane stream (13) drawn from the deisobutanizer column (27) is passed through a heat exchanger, mixed with an ethylene-rich stream (20) from the cracker (30) and the isobutane/ethylene mixture (14) is fed to the transhydrogenation reactor (29). In the transhydrogenation reactor (29) the isobutane, or portion thereof, is dehydrogenated to isobutene and the ethylene, or portion thereof, is hydrogenated to ethane by passage over a transhydrogenation catalyst, for example chromia on alumina, at an elevated temperature, for example 450° to 550° C.

The product stream (15) from the transhydrogenation reactor (29), comprising mainly a mixture of isobutene, ethane, isobutane and ethylene, is heat-exchanged with the isobutane feed (13), compressed and cooled in unit (31) and then fed (16) to debutanizer column (32) where it is separated into an ethane-rich $C_2$-hydrocarbon stream (17) and an isobutene-rich $C_4$-hydrocarbon stream (23).

The ethane-rich $C_2$-hydrocarbon stream (17) is recycled to the cracker (30), optionally after hydrotreatment to hydrogenate unsaturated compounds, and together with the make-up feed (18) is cracked to give the ethylene-rich stream (20), fuel gas (19), $C_3$ and heavier hydrocarbons (21) and water (22).

The isobutene-rich $C_4$-hydrocarbon stream (23) from the debutanizer column (32) and methanol (25) are fed to the etherification unit (33). In the etherification unit (33) methanol and isobutene are reacted, for example in the liquid phase over a solid phase strong acid ion-exchange resin catalyst, to give methyl t-butyl ether. A mixture of excess methanol and methyl t-butyl ether (26) is withdrawn from the etherification reactor (33) and distilled to give a methanol/methyl t-butyl ether azeotrope, which may be recycled to the etherification reactor, and methyl t-butyl ether as product which may be further purified by distillation as required. A gaseous mixture (24) mainly comprising isobutane is withdrawn from the etherification reactor (33) and recycled to the deisobutanization unit (27).

Table 1 below illustrates typical mass balances required to yield 100 parts by weight of methyl t-butyl ether using an isobutane/n-butane feed (11) and ethane as the make-up stream (18) to the cracker (30) in the procedure illustrated in FIG. 1.

gas being better cracker feedstock than liquified petroleum gas itself. Moreover, ethane, and most favoured feedstock for the production of ethylene, formed during the transhydrogenation reaction may be recycled (17) to the cracker (30) as feedstock, preferably after hydrotreatment to remove unsaturated compounds. Isobutene is usually formed during hydrocarbon cracking and any isobutene formed during cracking may be added to the isobutene-rich $C_4$-hydrocarbon stream (23). Therefore, combining and interconnecting a hydrocarbon cracker, a transhydrogenation reactor and an etherification reactor results in an integrated, economic process for the production of methyl t-butyl ether from liquified petroleum gas.

Figure 2:
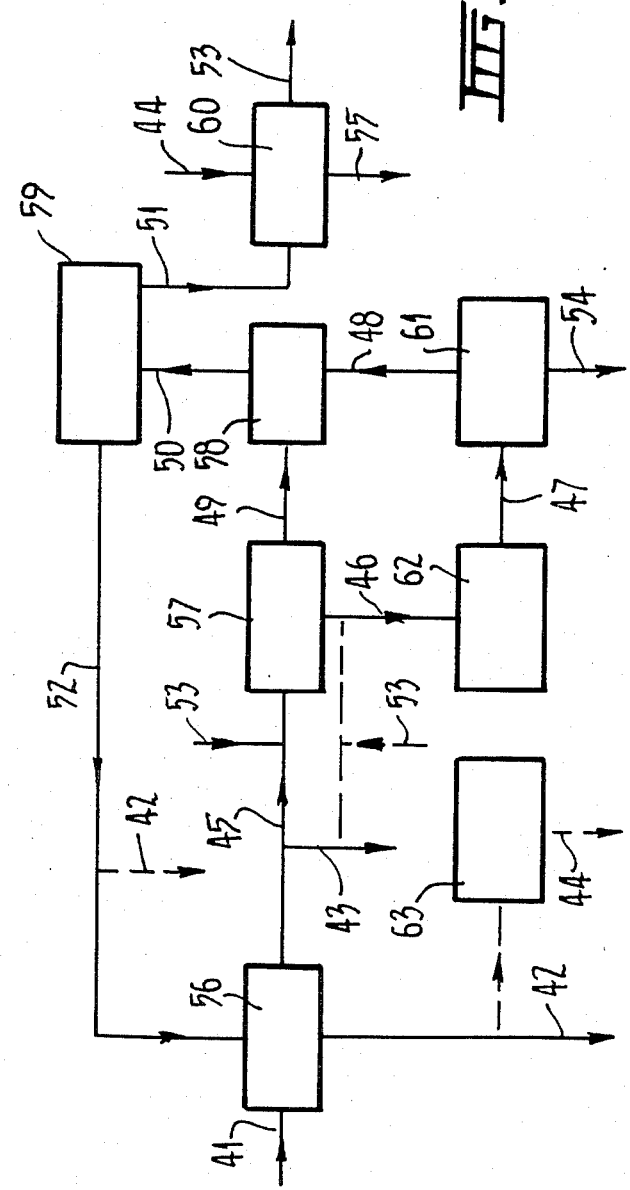
FIG. 2 is a schematic flow diagram of a plant for the production of MTBE utilizing gas from a natural gas field and incorporating a separation unit to separate the gas into natural gas for use in the preparation of methanol and liquid petroleum gas for use as a source of isobutene and cracker feedstock.

Referring to FIG. 2 of the drawings, a gas/liquids mixture (41) from a gas field is supplied to a gas/liquids separator (56) and separated into natural gas (42) and liquid petroleum gas (43). Optionally, all or portion of the natural gas (42) is supplied to a methanol plant (63) for conversion to methanol (44).

Portion of the liquid petroleum gas stream (45) is fed to a deisobutanizer column or selective adsorption unit (57) where it is separated into an isobutane-rich stream (49) and an n-butane-rich stream (46). The n-butane-rich stream (46) is fed to the cracker (62) where it is cracked to give an ethylene-rich product stream (47) which is fed to a separation stage (61) in which hydrogen, water and condensible hydrocarbons are removed (54) to give an ethylene-rich stream (48). Optionally, depending on the cracker requirements, portion of the n-butane-rich stream (46) may be returned to the liquid petroleum gas product stream (43).

The isobutane-rich stream (49) and ethylene-rich stream (48) are fed to the transhydrogenation reactor (58). In the transhydrogenation reactor (58) the isobutane, or portion thereof, is dehydrogenated to isobutene and the ethylene, or portion thereof, is hydrogenated to ethane by passage over a transhydrogenation catalyst, for example chromia on alumina, at an elevated temperature, for example 450° to 550° C.

The product stream (50) from the transhydrogenation reactor (58), comprising mainly a mixture of isobutene, ethane, isobutane and ethylene is fed to a debutanizer column (59) where it is separated into an ethane-rich $C_2$-hydrocarbon stream (52) and an isobutene-rich $C_4$-hydrocarbon stream (51).

The ethane-rich $C_2$-hydrocarbon stream (52) is recy-

TABLE 1

| Component | Contents (parts by weight) of Stream No (see FIG. 1) | | | | | | | | | | | | | | |
|---|---|---|---|---|---|---|---|---|---|---|---|---|---|---|---|
| | 11 | 12 | 13 | 14 | 15 | 16 | 17 | 18 | 19 | 20 | 22 | 23 | 24 | 25 | 26 |
| $H_2$ | — | — | — | — | — | — | — | — | 2.4 | — | — | — | — | — | — |
| $CH_4$ | — | — | — | — | 0.4 | 0.4 | 0.4 | — | 4.4 | — | — | — | — | — | — |
| $C_2H_4$ | — | — | — | 33.1 | 1.0 | 1.0 | 1.0 | — | — | 33.1 | — | — | — | — | — |
| $C_2H_6$ | — | — | 0.3 | 15.8 | 47.7 | 47.7 | 47.4 | 9.7 | — | 15.5 | — | 0.3 | 0.3 | — | — |
| $C_3$ | — | — | 2.2 | 3.5 | 4.4 | 4.4 | 2.2 | — | — | 1.3 | 1.5 | 2.2 | 2.2 | — | — |
| i-$C_4H_8$ | — | 0.1 | 0.5 | 0.5 | 64.8 | 64.8 | 0.3 | — | — | — | — | 64.5 | 0.6 | — | — |
| i-$C_4H_{10}$ | 70.4 | 2.7 | 135.7 | 135.7 | 69.2 | 69.2 | 0.6 | — | — | — | — | 68.7 | 67.9 | — | 0.7 |
| n-$C_4H_{10}$ | 85.8 | 85.5 | 1.4 | 1.4 | 1.4 | 1.4 | — | — | — | — | 1.1 | 1.3 | 1.3 | — | — |
| $C_{5+}$ | — | — | — | — | — | — | — | — | — | — | 2.2 | — | — | — | — |
| Coke | — | — | — | — | 1.2 | — | — | — | — | — | — | — | — | — | — |
| $CH_3OH$ | — | — | — | — | — | — | — | — | — | — | — | — | — | 37.6 | 0.7 |
| MTBE | — | — | — | — | — | — | — | — | — | — | — | — | — | — | 100 |

The process of the present invention illustrated in FIG. 1 has many advantages over prior-art processes for the manufacture of methyl t-butyl ether. Liquified petroleum gas (11) may be used both as a source of isobutane (13) and make-up feed (18) for the cracker (30), the essentially isobutane-free liquified petroleum cled to the gas/liquids separator (56) or, optionally, may be combined with the natural gas stream (42).

The isobutene rich $C_4$-hydrocarbon stream (51) and methanol (44) are fed into the etherification unit (60). In the etherification unit (60) methanol and isobutene are reacted, for example in the liquid phase over a solid phase strong ion-exchange resin catalyst, to give methyl t-butyl ether. A liquid phase mixture (55) comprising methanol and methyl t-butyl ether is withdrawn from the etherification reactor (60) and distilled to give a methanol/methyl t-butyl ether azeotrope which may be recycled to the etherification reactor and methyl t-butyl ether as product which may be further purified by distillation as required. A gaseous mixture (53) comprising mainly isobutane is withdrawn from the etherification reactor (60) and recycled to the deisobutanization unit (57) or, optionally, added to the liquid petroleum gas stream (43).

Table 2 below illustrates typical mass balances required to yield 100 parts by weight of methyl t-butyl ether using a gas/liquids feed (41) in the procedure illustrated in FIG. 2.

drogenation reactor (84). In the transhydrogenation reactor (84) the isobutane, or portion thereof, is dehydrogenated to isobutene and the ethylene, or portion thereof, is hydrogenated to ethane as hereinbefore described.

The product stream (75) from the transhydrogenation reactor (84) is combined with any isobutene containing stream (76) from refinery operations and fed into a debutanizer column (85) in which it is separated into an ethane-rich $C_2$-hydrocarbon stream (77), which is recycled for further refinery processing or fuel use, and an isobutene-rich $C_4$-hydrocarbon stream (78).

The isobutene-rich $C_4$-hydrocarbon stream (78) is combined with any other isobutene-rich stream (79) obtained from refinery operations and together with methanol (80) is fed into the etherification unit (86). In the etherification unit (86) methanol and isobutene are reacted as hereinbefore described to give methyl t-butyl

TABLE 2

| Component | Contents (parts by weight) of Stream No (see FIG. 2) | | | | | | | | | | | | | | |
|---|---|---|---|---|---|---|---|---|---|---|---|---|---|---|---|
| | 41 | 42 | 43 | 44 | 45 | 46 | 47 | 48 | 49 | 50 | 51 | 52 | 53 | 54 | 55 |
| $H_2$ | — | — | — | — | — | — | 2.4 | — | — | — | — | — | — | 2.4 | — |
| $CH_4$ | $1 \times 10^4$ | $1 \times 10^4$ | — | — | — | — | 13.2 | 13.2 | — | 13.6 | — | 13.6 | — | — | — |
| $C_2H_4$ | — | — | — | — | — | — | 33.1 | 33.1 | — | 1.0 | — | 1.0 | — | — | — |
| $C_2H_6$ | 1805 | 54 | 1751 | — | 213 | 20.7 | 15.5 | 15.5 | 0.3 | 47.7 | — | 47.7 | — | — | — |
| $C_3$ | 2426 | — | 2426 | — | 295 | 28.7 | 2.8 | 2.8 | 2.2 | 5.9 | 2.9 | 2.9 | 2.9 | — | — |
| $i\text{-}C_4H_{10}$ | 1121 | — | 1121 | — | 136 | 0.6 | — | — | 135.7 | 69.2 | 68.6 | 0.6 | 67.9 | — | 0.7 |
| $i\text{-}C_4H_8$ | — | — | — | — | — | — | — | — | 0.5 | 64.8 | 64.5 | 0.3 | 0.8 | — | — |
| $n\text{-}C_4H_{10}$ | 1678 | — | 1678 | — | 204 | 19.8 | — | 1.1 | 1.4 | 2.5 | 2.5 | — | 2.5 | — | — |
| $C_{5+}$ | — | — | — | — | — | — | 2.2 | — | — | — | — | — | — | 2.2 | — |
| Coke | — | — | — | — | — | — | — | — | — | 1.2 | — | — | — | — | — |
| Methanol | — | — | — | 37.6 | — | — | — | — | — | — | — | — | — | — | 0.7 |
| MTBE | — | — | — | — | — | — | — | — | — | — | — | — | — | — | 100 |

The process of the present invention illustrated in FIG. 2 has essentially the same advantages over prior art processes for the manufacture of methyl t-butyl ether as those detailed for the process illustrated in FIG. 1. However, in addition the process illustrated in FIG. 2 has greater flexibility as the ethane produced in the transhydrogenation process (52) can be recycled to the gas/liquids separator (56), added to the natural gas stream (42) or recycled to the cracker (62) as feedstock. Moreover, the isobutane-rich stream (53) from the etherification reactor (60) can either be recycled to the deisobutanizer column (57) or added to the liquified petroleum gas product stream (43).

The process of the present invention may also be used to advantage when the cracking facility produces ethylene as a by-product only. For example, in refining crude oil to manufacture petroleum products such as gasoline, "light gas" streams containing ethylene are also produced. Such olefin-rich refinery light gases are often reacted with light naphtha or low octane streams to give a higher yield of liquid hydrocarbons having a higher octane number. The present invention provides a process for more effective use of olefin-rich refinery light gases as the preparation of methyl t-butyl ether provides a relatively higher yield of liquid products and a relatively greater increase in octane number.

Figure 3:
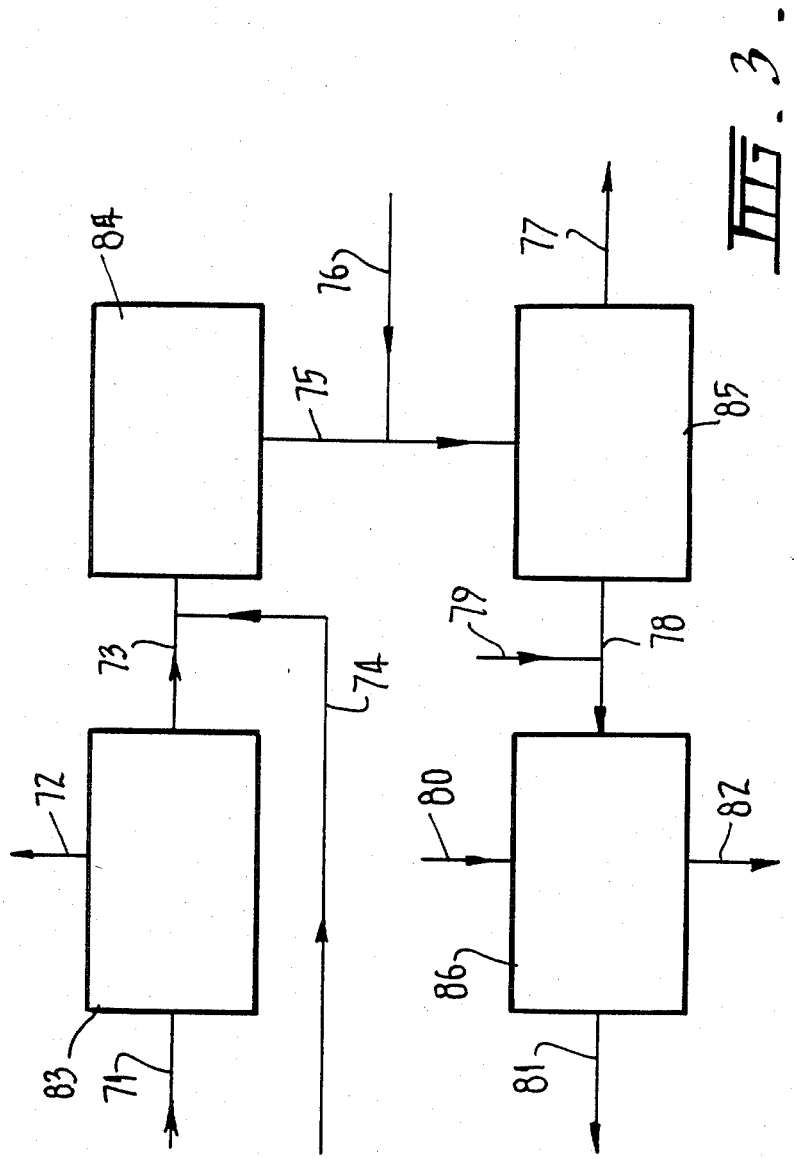
FIG. 3 is a schematic flow diagram of a plant for the production of MTBE using ethylene produced in an oil refinery, during the cracking of crude oil to produce petroleum products, in the transhydrogenation of isobutane to isobutene.

Referring to FIG. 3 of the drawings, a refinery dry gas stream (71) comprising hydrogen, carbon oxides, methane, ethane, propane and a significant proportion (>10% w/w) of ethylene is fed into a hydrogen recovery unit (83) and hydrogen (72) is separated and recycled for refinery operations. The olefin-enriched stream (73) is combined with an isobutane-rich stream (74) obtained from refinery product streams or by separation from liquified petroleum gas and fed into a transhyether. A liquid phase mixture (82) comprising methanol and methyl t-butyl ether is withdrawn from the reactor and distilled to give a methanol/methyl t-butyl ether azeotrope which may be recycled to the etherification reactor and methyl t-butyl ether as product which may be further purified by distillation as required. A gaseous mixture (81) comprising mainly isobutane is withdrawn from the etherification reactor (86) and recycled for recovery and combination with the isobutane rich stream (74).

The transhydrogenation step of the process of the present invention is now illustrated by, but in no way limited to, the following Examples.

EXAMPLES 1 TO 3

An approximately equimolar mixture of isobutane and ethylene was passed through a bed of a standard 19% w/w chromium oxide on alumina dehydrogenation catalyst (Harshaw Cr 0221T available from the Harshaw Chemical Company) in a tube furnace. The reaction conditions and composition of the inlet and outlet gas streams are given in Table 3 below.

TABLE 3

| | Example | | |
|---|---|---|---|
| | 1 | 2 | 3 |
| Reaction Conditions | | | |
| Temperature (°C.) | 400 | 450 | 480 |
| Pressure | atmospheric | atmospheric | atmospheric |
| Space Velocity | 0.85 | 0.85 | 0.85 |
| Inlet Gas Composition (mole %) | | | |
| Ethylene | 47.72 | 48.67 | 53.84 |
| Ethane | 0.10 | 0.10 | 0.11 |

TABLE 3-continued

| | Example | | |
|---|---|---|---|
| | 1 | 2 | 3 |
| Isobutane | 52.18 | 51.23 | 46.04 |
| Outlet Gas Composition (mole %) | | | |
| Hydrogen | 0.41 | 0.52 | 0.57 |
| Carbon Monoxide | 0.01 | 0.08 | 0.19 |
| Carbon Dioxide | 0.04 | 0.13 | 0.04 |
| Methane | 0.01 | 0.16 | 0.33 |
| Ethylene | 46.47 | 43.17 | 42.14 |
| Ethane | 1.17 | 6.06 | 12.09 |
| Propylene | 0 | 0.06 | 0.13 |
| Propane | 0.01 | 0.01 | 0.03 |
| Isobutane | 50.98 | 44.83 | 36.23 |
| Isobutene | 0.76 | 4.78 | 8.11 |
| Other $C_4$-Hydrocarbons | 0.07 | 0.15 | 0.11 |
| Higher Hydrocarbons | 0.06 | 0.05 | 0.03 |

EXAMPLES 4 TO 6

An approximately equimolar mixture of isobutane and ethylene was passed through a bed of a standard 14.9% w/w molybdenum oxide on alumina dehydrogenation catalyst (Harshaw Mo 205-1-R available from The Harshaw Chemical Company) in a tube furnace. The reaction conditions and composition of the inlet and outlet gas streams are given in Table 4 below.

TABLE 4

| | Example | | |
|---|---|---|---|
| | 4 | 5 | 6 |
| Reaction Conditions | | | |
| Temperature (°C.) | 400 | 450 | 480 |
| Pressure | atmospheric | atmospheric | atomspheric |
| Space Velocity (wrtsv; $h^{-1}$) | 1.4 | 1.4 | 1.4 |
| Inlet Gas Composition (mole %) | | | |
| Ethylene | 50.45 | 49.36 | 49.33 |
| Ethane | 0.10 | 0.10 | 0.10 |
| Isobutane | 49.45 | 50.54 | 50.57 |
| Outlet Gas Composition (mole %) | | | |
| Hydrogen | 0.16 | 2.07 | 2.02 |
| Carbon Monoxide | 0.12 | 0.28 | 0.43 |
| Carbon Dioxide | 0.34 | 0.23 | 0.06 |
| Methane | 0.08 | 0.50 | 0.73 |
| Ethylene | 49.80 | 42.61 | 43.74 |
| Ethane | 3.65 | 6.89 | 5.52 |
| Propylene | 0.10 | 0.33 | 0.37 |
| Propane | 0.02 | 0.03 | 0.03 |
| Isobutane | 45.11 | 44.87 | 45.16 |
| Isobutene | 0.55 | 1.65 | 1.63 |
| Other $C_4$-Hydrocarbons | 0.06 | 0.44 | 0.31 |
| Higher Hydrocarbons | 0.02 | 0.09 | 0.02 |

EXAMPLE 7

An approximately 2:1 molar mixture of isobutane and ethylene was passed through a bed of a standard 10% chromia on alumina catalyst (Katalysator G-41P available from Nissan Girdler Catalyst Co Ltd) in a tube furnace. The reaction conditions and composition of the inlet and outlet gas streams are given in Table 5 below.

TABLE 5

| Reaction Conditions | |
|---|---|
| Temperature (°C.) | 500 |
| Pressure | atmospheric |
| Inlet Gas Flow Rates ($cm^3 min^{-1}$) | |
| Ethylene | 6.0 |
| Isobutene | 12.0 |
| Outlet Gas Composition (mole %) | |
| Methane | 0.53 |
| Ethylene | 6.58 |
| Ethane | 25.38 |
| Propane | 0.62 |
| Isobutane | 45.78 |
| Isobutene | 21.11 |

I claim:

1. A process for the manufacture of methyl t-butyl ether which process comprises the following steps:
   (i) cracking a hydrocarbon feedstock in a cracking facility to give an ethylene-rich stream;
   (ii) separating an isobutane enriched stream from a $C_4$-hydrocarbon stream and optionally isomerizing the n-butane and recycling the resulting $C_4$-hydrocarbon stream for separation;
   (iii) contacting a mixture comprising the ethylene-rich stream from step (i) and the isobutane enriched stream from step (ii) with a transhydrogenation catalyst to give a hydrocarbon mixture comprising isobutene and ethane;
   (iv) either first separating the hydrocarbon mixture obtained in step (iii) into a $C_4$-hydrocarbon enriched stream comprising isobutene and a $C_2$-hydrocarbon enriched stream comprising ethane and second reacting said $C_4$-hydrocarbon enriched stream comprising isobutene with methanol to give methyl t-butyl ether and a residual $C_4$-hydrocarbon stream; or first reacting said mixture obtained in step (iii) with methanol to give methyl t-butyl ether and a residual hydrocarbon stream and optionally separating the residual hydrocarbon stream into a residual $C_4$-hydrocarbon stream and a $C_2$-hydrocarbon enriched stream; and
   (v) collecting the methyl t-butyl ether and recycling the residual $C_4$-hydrocarbon stream either to the $C_4$-hydrocarbon stream or to the cracking facility as feedstock and recycling the $C_2$-hydrocarbon enriched stream to the cracking facility or recycling the unseparated residual hydrocarbon stream to the cracking facility.

2. A process according to claim 1 wherein said cracking facility is a hydrocarbon cracker designed for the production of olefins.

3. A process according to claim 1 wherein said cracking facility is a refinery cracker designed to crack crude oil for the production of petroleum products.

4. A process according to claim 1 wherein said transhydrogenation catalyst is selected from metals and oxides of metals selected from the Groups IVA, VA, VIA, VIIA, VIII, and copper, zinc, gallium, indium, germanium, tin, lead, antimony, bismuth, tellurium and mixtures thereof.

5. A process according to claim 4 wherein said transhydrogenation catalyst is selected from the metals platinum, palladium, nickel, iridium, rhodium, cobalt, rhenium, ruthenium, iron and copper oxides of the metals chromium, molybdenum, copper, tungsten, titanium and zinc, and mixtures thereof.

6. A process according to claim 5 wherein said transhydrogenation catalyst is supported on a non-acidic porous carrier.

7. A process according to claim 6 wherein said transhydrogenation catalyst is a chromium oxide catalyst supported on a non-acidic alumina carrier.

8. A process according to claim 1 wherein in step (iii) said transhydrogenation process is carried out at a temperature in the range of from 400° to 550° C. and at a pressure in the range of 1.0 to 10 atmospheres.

9. A process according to claim 1 wherein in step (iv) said reaction between methanol and isobutene to give methyl t-butyl ether is carried out by contacting a liquid phase mixture comprising methanol and isobutene with a solid phase acidic catalyst.

10. A process for the manufacture of methyl t-butyl ether which process comprises the following steps:
 (i) cracking a hydrocarbon feedstock in a hydrocarbon cracker to give an ethylene-rich stream;
 (ii) separating a $C_4$-hydrocarbon stream into an isobutane enriched stream and an n-butane enriched stream in a de-isobutanizer unit, isomerizing the n-butane enriched stream in a catalytic isomerization reactor to give an isobutane/n-butane mixture, and recycling the isobutane/n-butane mixture to the deisobutanizer unit;
 (iii) reacting a mixture comprising the ethylene-rich stream from step (i) and the isobutane enriched stream from step (ii) over a chromium oxide on alumina transhydrogenation catalyst at a temperature in the range from 400° to 550° C. and at a pressure in the range of from 1.0 to 10 atmospheres to give a hydrocarbon mixture comprising isobutene and ethane;
 (iv) separating the hydrocarbon mixture from step (iii) into a $C_4$-hydrocarbon enriched stream comprising isobutene and a $C_2$-hydrocarbon enriched stream comprising ethane in a debutanizer column and reacting said $C_4$-hydrocarbon enriched stream with methanol in the liquid phase over an acidic solid phase catalyst to give methyl t-butyl ether and a residual $C_4$-hydrocarbon stream; and
 (v) recycling the $C_2$-hydrocarbon enriched stream to the hydrocarbon cracker, collecting the methyl t-butyl ether, and recycling the residual $C_4$-hydrocarbon stream to the $C_4$-hydrocarbon stream.

11. A process for the manufacture of methyl t-butyl ether which process comprises the following steps:
 (i) cracking a hydrocarbon feedstock in hydrocarbon cracker to give an ethylene-rich stream; p1 (ii) separating a $C_4$-hydrocarbon stream into an isobutane enriched stream and an n-butane enriched stream in a deisobutanizer unit and recycling the n-butane enriched stream to the hydrocarbon cracker for use as feedstock;
 (iii) reacting a mixture comprising the ethylene-rich stream from step (i) and the isobutane enriched stream from step (ii) over a chromium oxide on alumina transhydrogenation catalyst at a temperature in the range from 400° to 550° C. and at a pressure in the range of from 1.0 to 10 atmospheres to give a hydrocarbon mixture comprising isobutene and ethane;
 (iv) separating the hydrocarbon mixture from step (iii) into a $C_4$-hydrocarbon enriched stream comprising isobutene and a $C_2$-hydrocarbon enriched stream comprising ethane in a debutanizer column and reacting said $C_4$-hydrocarbon enriched stream with methanol in the liquid phase over an acidic solid phase catalyst to give methyl t-butyl ether and a residual $C_4$-hydrocarbon stream; and
 (v) recycling the $C_2$-hydrocarbon enriched stream to the hydrocarbon cracker, collecting the methyl t-butyl ether, and recycling the residual $C_4$-hydrocarbon stream to the $C_4$-hydrocarbon stream.

12. A process for the manufacture of methyl t-butyl ether which process comprises the following steps:
 (i) separating hydrogen from a refinery dry gas stream obtained from a refinery hydrocarbon cracking process to give an ethylene enriched stream and recycling the hydrogen for refinery use;
 (ii) separating a $C_4$-hydrocarbon stream obtained from natural gas or refinery operations into an isobutane enriched stream and an n-butane enriched stream in a deisobutanizer unit and recycling the n-butane enriched stream for refinery use;
 (iii) reacting a mixture comprising the ethylene enriched stream from step (i) and the isobutane enriched stream from step (ii) over a chromium oxide on alumina transhydrogenation catalyst at a temperature in the range from 400° to 550° C. and at a pressure in the range from 1.0 to 10 atmospheres to give a hydrocarbon mixture comprising isobutene and ethane;
 (iv) separating the hydrocarbon mixture from step (iii) into a $C_4$-hydrocarbon enriched stream comprising isobutene and a $C_2$-hydrocarbon enriched stream comprising ethane in a debutanizer column and reacting said $C_4$-hydrocarbon enriched stream with methanol in the liquid phase over an acidic solid phase catalyst to give methyl t-butyl ether and a residual $C_4$-hydrocarbon stream; and
 (v) collecting the methyl t-butyl ether and recycling the $C_2$-hydrocarbon enriched stream and the residual $C_4$-hydrocarbon stream for refinery use.

* * * * *